United States Patent
Wang et al.

(10) Patent No.: US 12,094,114 B2
(45) Date of Patent: Sep. 17, 2024

(54) METHOD, SYSTEM, AND STORAGE MEDIUM FOR OPPORTUNISTIC SCREENING OF OSTEOPOROSIS USING PLAIN FILM CHEST X-RAY (CXR)

(71) Applicants: Ping An Technology (Shenzhen) Co., Ltd., Shenzhen (CN); Chang Gung Memorial Hospital, Linkou, Taoyuan (TW)

(72) Inventors: Fakai Wang, Bethesda, MD (US); Chang-Fu Kuo, Taoyuan (TW); Kang Zheng, Bethesda, MD (US); Shun Miao, Bethesda, MD (US); Yirui Wang, Bethesda, MD (US); Le Lu, Bethesda, MD (US)

(73) Assignees: PING AN TECHNOLOGY (SHENZHEN) CO., LTD., Shenzhen (CN); Chang Gung Memorial Hospital, Linkou, Taoyuan (TW)

( * ) Notice: Subject to any disclaimer, the term of this patent is extended or adjusted under 35 U.S.C. 154(b) by 350 days.

(21) Appl. No.: 17/689,208

(22) Filed: Mar. 8, 2022

(65) Prior Publication Data

US 2022/0318996 A1    Oct. 6, 2022

Related U.S. Application Data

(60) Provisional application No. 63/165,231, filed on Mar. 24, 2021.

(51) Int. Cl.
G06T 3/40    (2024.01)
A61B 6/00    (2024.01)
(Continued)

(52) U.S. Cl.
CPC ............ *G06T 7/0012* (2013.01); *A61B 6/482* (2013.01); *A61B 6/505* (2013.01); *G06T 3/40* (2013.01);
(Continued)

(58) Field of Classification Search
CPC ....... A61B 6/482; A61B 6/505; A61B 6/5205; G06T 2207/10116; G06T 2207/20081;
(Continued)

(56) References Cited

U.S. PATENT DOCUMENTS 9,119,590 B2 *   9/2015   Budoff ................. A61B 6/5205
2003/0198316 A1 * 10/2003  Dewaele ................ G16H 15/00
378/54

(Continued)

OTHER PUBLICATIONS

Dildar Hussain, "Computer-aided osteoporosis detection from DXA imaging," Mar. 20, 2019, Computer Methods and Programs in Biomedicine 173, May,(2019), pp. 87-105.*

(Continued)

*Primary Examiner* — Omar S Ismail (57) ABSTRACT

A method of opportunistic screening of osteoporosis includes obtaining a plain film chest X-ray (CXR); extracting regions of interest (ROIs) from the plain film CXR; and providing individual bone mineral density (BMD) scores corresponding to the extracted ROIs and a joint BMD corresponding to the plain film CXR based on a multi-ROI model by performing: inputting the extracted ROIs into a backbone network to generate individual feature vectors, each individual feature vector corresponding to one of the extracted ROIs; concatenating the individual feature vectors into a joint feature vector; individually decoding the individual feature vectors by a shared fully connected (FC) layer to generate the individual BMDs, each individual BMD corresponding to one of the individual feature vectors; and
(Continued)

decoding the joint feature vector by a separate FC layer to generate the joint BMD.

18 Claims, 2 Drawing Sheets

(51) Int. Cl.
*A61B 6/50* (2024.01)
*G06T 7/00* (2017.01)
*G06V 10/25* (2022.01)

(52) U.S. Cl.
CPC .... *G06V 10/25* (2022.01); *G06T 2207/10116* (2013.01); *G06T 2207/20081* (2013.01); *G06T 2207/20084* (2013.01); *G06T 2207/30008* (2013.01); *G06V 2201/033* (2022.01)

(58) Field of Classification Search
CPC ........... G06T 2207/20084; G06T 2207/30008; G06T 3/40; G06T 7/0012; G06V 10/25; G06V 10/44; G06V 10/766; G06V 10/82; G06V 2201/033
See application file for complete search history.

(56) References Cited

U.S. PATENT DOCUMENTS

| | | | | |
|---|---|---|---|---|
| 2004/0241743 | A1* | 12/2004 | Nicholson | A61B 5/412 435/7.1 |
| 2005/0010106 | A1* | 1/2005 | Lang | A61B 6/4423 600/425 |
| 2005/0037515 | A1* | 2/2005 | Nicholson | G01R 33/465 436/173 |
| 2008/0082002 | A1* | 4/2008 | Wilson | A61B 5/7275 378/54 |
| 2008/0171319 | A1* | 7/2008 | Urdea | A61K 45/00 435/7.1 |
| 2011/0014620 | A1* | 1/2011 | Basilico | G01N 33/6872 435/6.1 |
| 2014/0081146 | A1* | 3/2014 | Keim | A61B 6/5241 600/407 |
| 2016/0015347 | A1* | 1/2016 | Bregman-Amitai | G06T 7/0012 382/131 |
| 2020/0402226 | A1* | 12/2020 | Peng | G06N 3/047 |
| 2021/0106286 | A1* | 4/2021 | Subramanian | A61B 5/7267 |
| 2021/0212647 | A1* | 7/2021 | Zheng | G06T 7/73 |

OTHER PUBLICATIONS

S.M. Nazia Fathima, "A Deep Learning Approach on Segmentation of Bone for BMD Measurement from DEXA Scan Images," Aug. 26, 2020, 2020 Sixth International Conference on Bio Signals, Images, and Instrumentation (ICBSII), pp. 1-4.*

Mirella López Picazo, "3-D Subject-Specific Shape and Density Estimation of the Lumbar Spine From a Single Anteroposterior DXA Image Including Assessment of Cortical and Trabecular Bone," Nov. 29, 2018, IEEE Transactions on Medical Imaging, vol. 37, No. 12, Dec. 2018, pp. 2651-2659.*

Anushikha Singh, "Classification of the trabecular bone structure of osteoporotic patients using machine vision," Oct. 20, 2017, Computers in Biology and Medicine, vol. 91, Dec. 1, 2017, pp. 149-157.*

Vimal Chandran, "Supervised learning for bone shape and cortical thickness estimation from CT images for finite element analysis," Nov. 16, 2018, Medical Image Analysis 52 (2019) 42, pp. 42-53.*

Perry J. Pickhardt, "Automated Abdominal CT Imaging Biomarkers for Opportunistic Prediction of Future Major Osteoporotic Fractures in Asymptomatic Adults," Jun. 10, 2020, radiology.rsna.org ,Radiology: vol. 297: No. 1—Oct. 2020, pp. 64-71.*

Mohsen Farzi, "A Spatio-Temporal Ageing Atlas of the Proximal Femur," Apr. 30, 2020, IEEE Transactions on Medical Imaging, vol. 39, No. 5, May 2020, pp. 1359-1367.*

* cited by examiner

METHOD, SYSTEM, AND STORAGE MEDIUM FOR OPPORTUNISTIC SCREENING OF OSTEOPOROSIS USING PLAIN FILM CHEST X-RAY (CXR)

CROSS-REFERENCE TO RELATED APPLICATION

This application claims the priority of U. S. Provisional Patent Application No. 63/165,231, filed on Mar. 24, 2021, the entire content of which is incorporated herein by reference.

FIELD OF THE TECHNOLOGY

This application relates to the field of medical image interpretation and, more particularly, to a method, a system, and a storage medium for opportunistic screening of osteoporosis using plain film chest X-ray (CXR).

BACKGROUND OF THE DISCLOSURE

Osteoporosis is the most common chronic metabolic bone disease, characterized by low bone mineral density (BMD) and decreased bone strength to resist pressure or squeeze force. With an aging population and longer life span, osteoporosis is becoming a global epidemic, affecting more than 200 million people worldwide. Osteoporosis increases the risk of fragility fractures, which is associated with reduced life quality, disability, fatality, and financial burden to patient families and the society. While with an early diagnosis and treatment, osteoporosis can be prevented or managed, osteoporosis is often under-diagnosed and under-treated among the population at risk. More than half of insufficiency fractures occur in individuals who have never been screened for osteoporosis. The under-diagnosis and under-treatment of osteoporosis are mainly due to low osteoporosis awareness and limited accessibility of Dual-energy X-ray Absorptiometry (DXA) examination, which is the currently recommended modality to measure the BMD.

SUMMARY

One aspect of the present disclosure provides a method of opportunistic screening of osteoporosis. The method includes: obtaining a plain film chest X-ray (CXR); extracting regions of interest (ROIs) from the plain film CXR; and providing individual bone mineral density (BMD) scores corresponding to the extracted ROIs and a joint BMD corresponding to the plain film CXR based on a multi-ROI model by performing: inputting the extracted ROIs into a backbone network to generate individual feature vectors, each individual feature vector corresponding to one of the extracted ROIs; concatenating the individual feature vectors into a joint feature vector; individually decoding the individual feature vectors by a shared fully connected (FC) layer to generate the individual BMDs, each individual BMD corresponding to one of the individual feature vectors; and decoding the joint feature vector by a separate FC layer to generate the joint BMD.

Another aspect of the present disclosure provides a system of opportunistic screening of osteoporosis using plain film chest X-ray images. The system includes a memory storing a computer program; and a processor configured to execute the computer program stored in the memory to: obtain a plain film chest X-ray (CXR); extract regions of interest (ROIs) from the plain film chest x-ray; and provide individual bone mineral density (BMD) scores corresponding to the extracted ROIs and a joint BMD corresponding to the plain film CXR based on a multi-ROI model by performing: inputting the extracted ROIs into a backbone network to generate individual feature vectors, each individual feature vector corresponding to one of the extracted ROIs; concatenating the individual feature vectors into a joint feature vector; individually decoding the individual feature vectors by a shared fully connected (FC) layer to generate the individual BMDs, each individual BMD corresponding to one of the individual feature vectors; and decoding the joint feature vector by a separate FC layer to generate the joint BMD.

Another aspect of the present disclosure provides a storage medium storing a computer program. When being executed by a processor, the computer program performs: obtaining a plain film chest X-ray (CXR); extracting regions of interest (ROIs) from the plain film CXR; and providing individual bone mineral density (BMD) scores corresponding to the extracted ROIs and a joint BMD corresponding to the plain film CXR based on a multi-ROI model by performing: inputting the extracted ROIs into a backbone network to generate individual feature vectors, each individual feature vector corresponding to one of the extracted ROIs; concatenating the individual feature vectors into a joint feature vector; individually decoding the individual feature vectors by a shared fully connected (FC) layer to generate the individual BMDs, each individual BMD corresponding to one of the individual feature vectors; and decoding the joint feature vector by a separate FC layer to generate the joint BMD.

Other aspects of the present disclosure can be understood by those skilled in the art in light of the description, the claims, and the drawings of the present disclosure.

DETAILED DESCRIPTION

The following describes the technical solutions in the embodiments of the present invention with reference to the accompanying drawings. Wherever possible, the same reference numbers will be used throughout the drawings to refer to the same or like parts. Apparently, the described embodiments are merely some but not all the embodiments of the present invention. Other embodiments obtained by a person skilled in the art based on the embodiments of the present invention without creative efforts shall fall within the protection scope of the present disclosure.

Opportunistic screening of osteoporosis is an emerging research field in recent years. It aims at using medical images done for other indications to screen for osteoporosis, which offers an opportunity to increase the screening rate at no additional cost or time. Previous attempts mainly focused on using computed tomography (CT) scans (i.e., Hounsfield unit) of the vertebrae to correlate with bone mineral density (BMD) and/or fracture risk. Plain films have much greater accessibility than CT scans. Its excellent spatial resolution permits the delineation of fine bony microstructure that may contain information correlating well with the BMD. In the present disclosure, a standard chest X-ray (CXR) image, the most common medical imaging prescribed clinically, is used for opportunistic screening of osteoporosis. Specifically, regions of interest (ROI) in the CXR image are for opportunistic screening of osteoporosis.

The present disclosure provides a method for estimating BMD from CXR image for screening osteoporosis. At first, anatomical landmarks of patient's bone structures are located and multiple ROIs are extracted to provide biomarkers for osteoporosis. A novel network architecture that jointly processes the ROIs is provided to accurately estimate the BMD. The method is evaluated against 1,651 CXR images from 1,638 patients with ground truth BMDs measured using Dual-energy X-ray Absorptiometry (DXA). The evaluation results show that the BMDs estimated from the CXR images achieve a high correlation with the DXA BMD (i.e., a Pearson correlation coefficient R-value of 0.840) and a high osteoporosis diagnosis (i.e., an area under curve or AUC score of 0.936). Therefore, the method for estimating the BMD from the CXR image becomes a practical solution for opportunistic screening of osteoporosis.

The method consistent with the present disclosure combines global and local information in the CXR to accurately estimate bone BMDs, substantially outperforms baseline methods and achieves clinically useful osteoporosis screening performance. In some embodiments, the bone BMDs may include lumbar spine BMDs, hip bone BMDs, and other suitable bone BMDs. For convenience of description, the lumbar spine BMDs are used in the specification. However, the present disclosure is not limited to the estimation of the lumbar spine BMDs using the plain film CXR.

Figure 1:
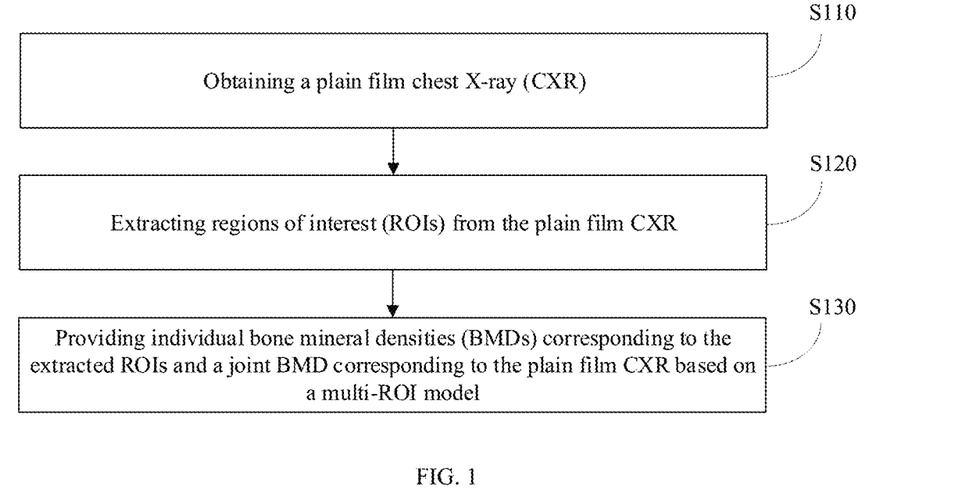
FIG. 1 illustrates a flowchart of an exemplary method of screening osteoporosis using plain film chest X-ray (CXR) consistent with embodiments of the present disclosure.

FIG. 1 illustrates a flowchart of an exemplary method of screening osteoporosis using plain film chest X-ray (CXR) consistent with embodiments of the present disclosure. As shown in FIG. 1, the method includes the following processes.

At S110, a plain film CXR is obtained.

In some embodiments, the plain film CXR is a frontal chest X-ray image including the patient's lumber spine. The lumbar spine is chosen to predict the BMD because the lumbar spine is one of standard regions for BMD examination and is often affected by insufficiency fracture. Predicting the BMDs of the patient's lumbar spine is formulated as a regression problem. The input is the CXR and the output is a predicted BMD. However, the lumber spine is not visible in the CXR. It is difficult to identify regions and visual patterns in the CXR that are correlated with the lumbar spine BMDs. The method consistent with the present disclosure includes two parts. In the first part, regions of interest (ROIs) that are potentially correlated with the lumbar spine BMDs are extracted. In the second part, a trained multi-task regression neural network is used to jointly analyze the ROIs to predict the BMDs.

At S120, regions of interest (ROIs) are extracted from the plain film CXR.

Generally, it is unclear which local regions within the CXR are most informative for estimating the BMDs. In some embodiments, correlations between the lumbar spine BMDs and different regions in the CXR are explored by extracting multiple ROIs. The extracted ROIs include different scales to explore both local textures and global structures. Because osteoporosis is a metabolic bone disease that affects all bones in a human body, bone regions in the CXR provide visual cues of the lumbar spine BMDs. In some embodiments, the extracted ROIs include six regions of local bone structures/patterns: left/right clavicle bones, cervical spine, left/right rib-cage area, and T12 vertebra. The extracted ROIs further include the entire CXR for global structural information. In some other embodiments, the extracted ROIs may include other regions of local bone structures/patterns. A landmark detection method is used to automatically extract the ROIs.

In some embodiments, the landmark detection method may be a graph-based landmark detection method. For example, the landmark detection method is a deep adaptive graph (DAG) method. The landmarks are modeled as a graph. Global-to-local cascaded graph convolutional networks (GCNs) are employed in the DAG method to move the landmarks towards targets in multiple steps. Graph signals of the landmarks are built by combining local image features and graph shape features. Two GCNs operate in a cascaded manner, with the first GCN estimating a global transformation of the landmarks and the second GCN estimating local offsets to further adjust the landmark coordinates. The graph topology, represented by connectivity weights between the landmarks, are learned during a training phase. The present disclosure is not limited to using DAG method to extract the ROIs. Another landmark detection method may be used to extract the ROIs.

In some embodiments, 16 landmarks are detected. The 16 landmarks include three points on the left/right clavicles, four points along the left/right ribcages, one point on the cervical spine, and one point on the T12 vertebra. The ROIs are placed based on the detected landmarks. Examples of the CXR with the 16 landmarks and the corresponding extracted ROIs are shown in FIG. 2.

At S130, individual bone mineral density (BMD) scores are provided corresponding to the extracted ROIs based on a multi-ROI model.

Figure 2:
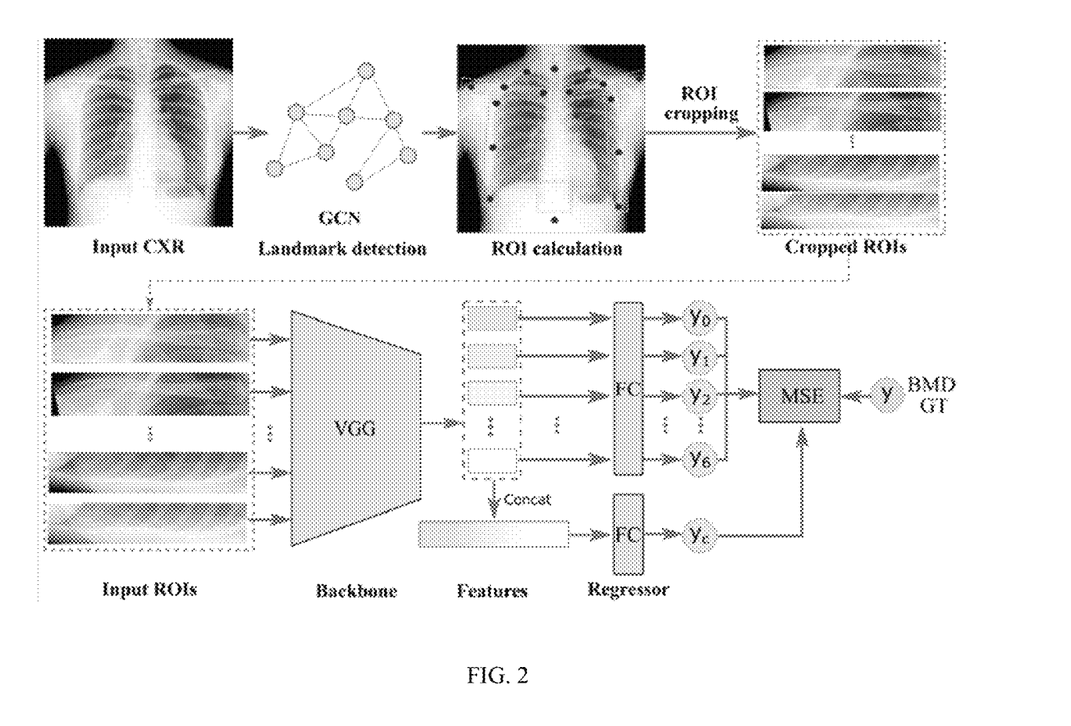
FIG. 2 illustrates a schematic diagram of multi-ROI model training workflow consistent with embodiments of the present disclosure.

FIG. 2 illustrates a schematic diagram of multi-ROI model training workflow consistent with embodiments of the present disclosure. A landmark detector localizes 16 dots in the CXR to anchor local bones in a plurality of dotted line boxes. Each dotted line box is normalized to a same orientation and a same height-to-width ratio and is cropped into the extracted ROIs. The extracted ROIs are then processed by the multi-ROI model.

In some embodiments, the multi-ROI model includes six local ROIs and one whole chest image as independent inputs. In a process of training the multi-ROI model, a mean square error loss (MSE) is calculated to generate seven individual feature BMD predictions $y_0, y_1, y_2, y_3, y_4, y_5, y_6$. Further, the seven ROIs are concatenated and processed to generate a concatenated feature BMD prediction $y_c$. The seven ROIs are jointly analyzed by the multi-ROI model to estimate the BMDs of the lumbar spine.

The multi-ROI model is a multi-task learning network capable of extracting visual patterns at different scales that are informative for estimating or predicting the BMDs of the lumber spine. The multi-ROI model includes a visual geometry group 16-layer (VGG-16) neural network as its backbone network to generate a feature map encoding of the input ROIs and apply global average pooling (GAP) to aggregate the feature map to a single feature vector. The seven ROIs go through the same VGG-16 neural network independently, generating seven feature vectors. The seven feature vectors are then decoded both separately and jointly.

The seven feature vectors are individually processed by a shared fully connected (FC) layer to generate BMD estimates or scores. Then, the seven feature vectors are concatenated to obtain a concatenated feature vector or a joint feature vector, which is decoded by another FC layer to generate another BMD estimate. In the process of training the multi-ROI model, the MSE is calculated on the BMD estimates generated from the feature vectors of the individual ROIs and the BMD estimate generated from the concatenated feature vector. The average MSE is used as a training loss. In a process of testing the multi-ROI model, the BMD estimate generated from the concatenated feature vector is taken as an output.

The method consistent with the present disclosure is evaluated using CXRs from actual patients. A dataset of 1,651 frontal view CXRs is collected from a hospital with patient information removed. The CXRs are paired with the BMDs on four lumber vertebrae L1-L4. The evaluation uses a same data split in various scenarios, including 1,087 CXRs for training, 265 CXRs for validation, and 329 CXRs for testing. The CXRs of same patients are only included in a same split dataset.

Performance of the method is evaluated by a Pearson correlation coefficient (R-value) and an area under curve (AUC) score. The R-value measures the linear relationship between the BMD estimates and ground truth BMDs. It only considers the correlation between two sequences regardless of their absolute values. The AUC score measures accumulated true positive (osteoporosis) rate under different judging thresholds for binary classification. The AUC score is calculated under a T-score range instead of the BMDs as the T-score is widely adopted measurement in clinical practices. The BMD estimates are converted to the T-scores by checking a transforming table coming with a DXA machine. To evaluate osteoporosis diagnosis performance, the patient of a CXR is labeled as positive osteoporosis when the ground truth T-score paired with the CXR is below −2.5, which is the clinical definition of osteoporosis.

In some embodiments, the input CXR is resized to 256 by 256 and repeated three times to form RGB channels. Augmentations such as scaling, rotation, translation, random flip are applied during training. A stochastic gradient descent (SGD) optimizer having a learning rate of 0.0001 and a weight decay of 0.0004 is used to train the multi-ROI model. A mini-batch size of 64 is used to train the multi-ROI model for 100 epochs.

Performances of different backbone networks are evaluated using a baseline method. The baseline method takes the whole CXR as input, employs a backbone network as an encoder, and uses a GAP layer and a FC layer for regression. Table 1 shows performances of the multi-ROI model using different deep learning backbones. VGG-16 neural network has the best overall performance. Resnet provides complex feature computation and works better on classification tasks. The bone texture encoding task involves only low-level pattern recognition, where VGG networks or models fit better

TABLE 1

| Backbone | L1 | | L2 | | L3 | | L4 | | Average | |
| --- | --- | --- | --- | --- | --- | --- | --- | --- | --- | --- |
| | R-value | AUC | R-value | AUC | R-value | AUC | R-value | AUC | R-value | AUC |
| Vgg11 | 0.843 | 0.919 | 0.838 | 0.916 | 0.832 | 0.917 | 0.772 | 0.881 | 0.821 | 0.908 |
| Resnet18 | 0.759 | 0.875 | 0.799 | 0.863 | 0.774 | 0.852 | 0.717 | 0.840 | 0.762 | 0.858 |
| Resnet34 | 0.787 | 0.903 | 0.787 | 0.866 | 0.768 | 0.887 | 0.723 | 0.861 | 0.766 | 0.879 |
| Resnet50 | 0.799 | 0.894 | 0.823 | 0.888 | 0.795 | 0.880 | 0.741 | 0.858 | 0.789 | 0.880 |
| Vgg16 | 0.865 | 0.923 | 0.863 | 0.913 | 0.824 | 0.918 | 0.804 | 0.901 | 0.839 | 0.914 |

In Table 2, different ROIs are evaluated using the same VGG-16 neural network backbone. In the first five rows, single ROIs are used as input to a regression network to predict the BMIDs. The first four rows are results using local ROIs. The fifth row "chest" uses the whole chest image (global ROI model). The cervical models have the best performance among the local ROIs, reporting an R-value of 0.795 and an AUC score of 0.906. The fifth row "chest" performs better than all the local ROI models because the whole CXR contains the overall bone information. The sixth row is the multi-ROI model fed on all input modalities and has the best overall performance.

TABLE 2

| Modality | L1 | | L2 | | L3 | | L4 | | Average | |
| --- | --- | --- | --- | --- | --- | --- | --- | --- | --- | --- |
| | R-value | AUC | R-value | AUC | R-value | AUC | R-value | AUC | R-value | AUC |
| cervi | 0.823 | 0.915 | 0.817 | 0.930 | 0.802 | 0.937 | 0.738 | 0.841 | 0.795 | 0.906 |
| clavi | 0.793 | 0.893 | 0.778 | 0.917 | 0.745 | 0.867 | 0.709 | 0.857 | 0.756 | 0.883 |
| lumbar | 0.750 | 0.829 | 0.791 | 0.889 | 0.754 | 0.859 | 0.711 | 0.841 | 0.751 | 0.855 |
| ribcage | 0.748 | 0.868 | 0.768 | 0.876 | 0.730 | 0.850 | 0.703 | 0.830 | 0.737 | 0.856 |
| chest | 0.865 | 0.923 | 0.863 | 0.913 | 0.824 | 0.918 | 0.804 | 0.901 | 0.839 | 0.914 |
| Prop. | 0.875 | 0.936 | 0.857 | 0.944 | 0.843 | 0.941 | 0.783 | 0.924 | 0.840 | 0.936 |

The CXR includes many bones. The BMD of one bone may not be consistent with another. The individual ROI models lack a mechanism to solve conflicts of inconsistent BMDs from different bones. The multi-ROI model allows the neural network to automatically identify the informative regions for estimating the BMDBMDs of the lumbar spine.

Referring back to FIG. 2, the multi-ROI model takes seven input modalities all at once and the seven input modalities share the same encoding backbone network. Each encoded feature vector is of size 512. The concatenated feature vector has a shape of 512*7. The individual ROI feature vectors share the same FC layer while the concatenated feature vector goes through a separate stand-along FC layer.

Figure 3:
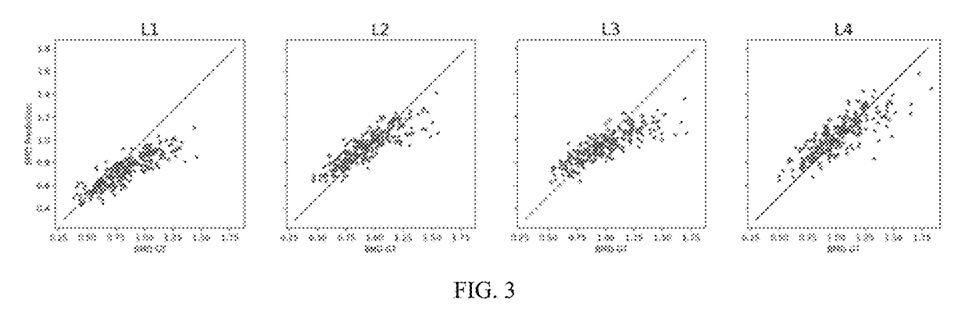
FIG. 3 illustrates schematic diagrams of multi-ROI model BMD prediction on different lumbar vertebra (L1-L4) consistent with embodiments of the present disclosure.

FIG. 3 illustrates schematic diagrams of multi-ROI model BMD prediction on different lumbar vertebra (L1-L4) consistent with embodiments of the present disclosure. X-axis is the ground truth BMD and Y-axis represents the predicted BMD. The estimated BMDs and the ground truth BMDs are plotted in FIG. 3. Compared to prediction distribution of other ROI models, the concatenated feature vector and the corresponding FC layer in the multi-ROI model tightens the prediction range, reducing predicting error variation. The shared FC layer enforces regularization on individual feature vectors, reducing absolute predicting errors.

The multi-ROI model achieves an average R-value of 0.840 and an average AUC score of 0.936, outperforming all individual ROI models in Table 2. Compared with the "chest" ROI model, the multi-ROI model encodes additional six local ROI modalities to allow for detailed local texture computation. The feature concatenation retains encoded information from both local ROIs and the global chest, involving regional information interactions. The multi-ROI model yields a higher AUC score than model ensembles in Table 3.

TABLE 3

| Ensemble | L1 | | L2 | | L3 | | L4 | | Average | |
| --- | --- | --- | --- | --- | --- | --- | --- | --- | --- | --- |
| | R-value | AUC | R-value | AUC | R-value | AUC | R-value | AUC | R-value | AUC |
| Ensm_roi | 0.879 | 0.935 | 0.876 | 0.946 | 0.850 | 0.929 | 0.812 | 0.894 | 0.854 | 0.926 |
| Ensm_all | 0.881 | 0.938 | 0.880 | 0.949 | 0.851 | 0.933 | 0.816 | 0.903 | 0.857 | 0.931 |

The individual model performance is influenced by data distribution, input modality choice, and training process. Overfitting is also a challenge due to the limited amount of labeled data. A common strategy to boost the model performance is ensemble learning. Table 2 includes six models using different ROI models. The average of the BMVD predictions from the six individual ROI models is used as ensemble predictions shown in Table 3. Ensemble_roi is an ensemble of all individual ROI models, that is, cervical, clavicle, lumbar, ribcage, and chest models. Ensemble_all is the ensemble of all models including the multi-ROI model.

Compared to Ensemble_roi, Ensemble_all includes the multi-ROI model and outperforms in all metrics. Although Ensemble_roi includes information from the local modalities and the whole CXR image, the simple average of the individual ROI model predictions lacks an adaptive feature fusion process. In the multi-ROI model, the concatenated feature vector and the corresponding FC layer exploit all regional information. Different importance of various regions is learned in the FC layer weights.

Even though both ensemble schemes perform better in terms of the average R-value, they do not exceed the multi-ROI model in terms of the average AUC score. A high R-value indicates high consistency of sequential order with the ground truth. A high AUC score indicates accurate osteoporosis diagnosis around the T-score threshold. The multi-ROI model has a substantially higher AUC score than any individual ROI model, proving its reliability to diagnose osteoporosis. The Ensemble_all does not improve the AUC score over the multi-ROI model. Thus, the average prediction from the individual ROI models is less accurate around the T-score threshold.

Further, it is observed that adjacent bones have more consistent BMDs while the correlation decreases as distances separating the adjacent bones increase. For example, in the BMD ground truth of the lumbar spine, L1 has the R-value of 0.907 to L2, and the R-value of 0.883 to L3, but only has the R-value of 0.825 to L4. Thus, the ROI model performance does not exceed the neighboring lumbar BMD R-values (such as L1 and L3).

The BMD prediction performance may also be compromised by physiological differences between lumbar bones and chest bones. The accuracy for cross-region BMD prediction has an upper limit due to osteoporosis distribution and bone differences. In Table 2, the cervical model performs the best and the ribcage model performs the worst among the local ROI models. The cervical vertebra provides a function similar to the lumbar in spine activity while bones in the ribcage ROIs remain stationary from body activities. The undesired performance of the lumbar ROI model is caused by X-ray overexposure and noise in the lumbar region of the frontal view CXR.

In the lumbar BMD ground truth, the L1 MBD score is generally smaller than the L2 BMD, the L2 BMD is generally smaller than the L3 BMD, and the L3 BMD is generally smaller than the L4 BMD. Referring to FIG. 3, the L1 BMD distribution has a much lower range than the L4 BMD. The multi-ROI model achieves the R-value of 0.875 and the AUC score of 0.936 on the L1 BMD prediction, which is close to the R-value between the ground truth BMDs of the L1 and L3 (i.e., 0.883). Thus, it validates the applicability of the disclosed method.

In the embodiments of the present disclosure, the BMDs are predicted or estimated from the CXRs. The multi-ROI model jointly analyzes multiple local and global ROIs from the CXR to predict the patient's lumbar spine BMDs and substantially outperforms the individual ROI models or the whole CXR model. Thus, the multi-ROI model can be applied to opportunistic screening of osteoporosis.

Figure 4:
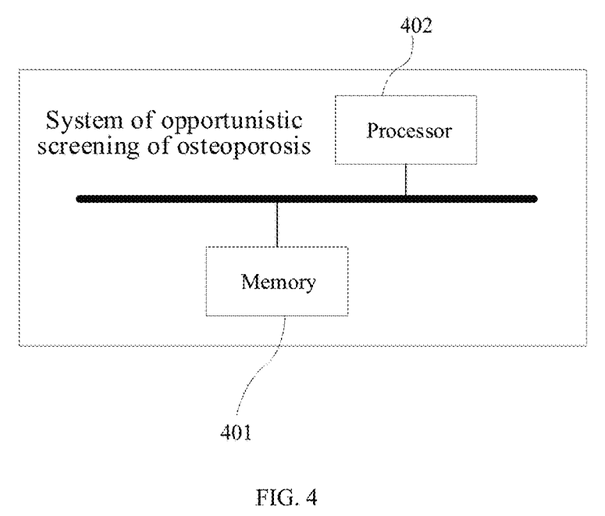
FIG. 4 illustrates a schematic structural diagram of an exemplary system of opportunistic screening of osteoporosis consistent with embodiments of the present disclosure.

FIG. 4 illustrates a schematic structural diagram of an exemplary system of opportunistic screening of osteoporosis consistent with embodiments of the present disclosure. Referring to FIG. 4, the present disclosure provides a system for estimating BMD from CXR for screening osteoporosis. The system performs the disclosed method for screening osteoporosis. In some embodiments, the system includes a memory 401 storing a computer program and a processor 402 configured to execute the computer program stored in the memory 401 to: obtain a plain film chest X-ray (CXR); extract regions of interest (ROIs) from the plain film chest x-ray; and provide individual bone mineral density (BMD) scores corresponding to the extracted ROIs and a joint BMD based on a multi-ROI model by performing: inputting the extracted ROIs into a backbone network to generate individual feature vectors, each individual feature vector corresponding to one of the extracted ROIs; concatenating the individual feature vectors into a joint feature vector; individually decoding the individual feature vectors by a shared fully connected (FC) layer to generate the individual BMDs, each individual BMD corresponding to one of the individual feature vectors; and decoding the joint feature vector by a separate FC layer to generate the joint BMD.

In some embodiments, the processor 402 is further configured to: perform training of the multi-ROI model based on a plurality of plain film CXRs each having a ground truth BMD measured by a dual-energy X-ray absorptiometry (DXA) machine, wherein the training of the multi-ROI model includes calculating mean squared errors (MSEs) on each of the individual BMDs and the joint BMD, and an average MSE thereof being used as a training loss.

In some embodiments, the ground truth BMD corresponding to each plain film CXR is measured by the DXA machine for spine bones or hip bones; in response to the multi-ROI model being trained based on the ground truth BMD for the spine bones, the BMD predicted by the multi-ROI model is the BMD for the spine bones; and in response to the multi-ROI model being trained based on the ground truth BMD for the hip bones, the BMD predicted by the multi-ROI model is the BMD for the hip bones.

In some embodiments, the processor 402 is further configured to perform an opportunistic screening of osteoporosis on a test plain film CXR, comprising: extracting ROIs from the test plain film CXR; providing a BMD corresponding to the test plain film X-ray image based on the trained multi-ROI model by performing: inputting the extracted ROIs into the backbone network to generate individual feature vectors, each individual feature vector corresponding to one of the extracted ROIs, and concatenating the individual feature vectors into a joint feature vector; and decoding the joint feature vector by the separate FC layer to generate the joint BMD, the joint BMD being the BMD corresponding to the test plain film CXR; converting the BMD corresponding to the test plain film CXR into a T-score; and in response to the T-score being smaller than or equal to a T-score threshold, determining a positive diagnosis of osteoporosis.

In some embodiments, the T-score threshold is −2.5.

In some embodiments, before extracting the ROIs from the plain film CXR, the processor 402 is further configured to resize the plain film CXR to a fixed size.

In some embodiments, the backbone network is a visual geometry group 16-layer (VGG-16) neural network.

In some embodiments, when extracting the ROIs from the plain film CXR, the processor 402 is further configured to: use a landmark detection method to automatically detect a plurality of landmarks in the plain film CXR; and based on the plurality of landmarks, extract the ROIs from the plain film CXR.

In some embodiments, the ROIs include a plurality of local regions in the plain film CXR and a global region including the entire plain film CXR.

In the embodiments of the present disclosure, the BMDs are predicted or estimated from the CXRs. The multi-ROI model jointly analyzes multiple local and global ROIs from the CXR to predict the patient's lumbar spine BMDs and substantially outperforms the individual ROI models or the whole CXR model. Thus, the multi-ROI model can be applied to opportunistic screening of osteoporosis.

The memory 401 may include volatile memory such as random-access memory (RAM), and non-volatile memory such as flash memory, hard disk drive (HDD), or solid-state drive (SSD). The memory 401 may also include combinations of various above-described memories. The processor 402 may include a central processing unit (CPU), an embedded processor, a microcontroller, and a programmable device such as an application-specific integrated circuit (ASIC), a field programmable gate array (FPGA), and a programmable logic array (PLD), etc.

The present disclosure also provides a non-transitory computer-readable storage medium storing a computer program. The computer program may be loaded to a computer or a processor of a programmable data processing device, such that when the computer program is executed by the computer or the processor of the programmable data processing device to implement the disclosed method. The description thereof is omitted.

Although the principles and implementations of the present disclosure are described by using specific embodiments in the specification, the foregoing descriptions of the embodiments are only intended to help understand the method and core idea of the method of the present disclosure. Meanwhile, a person of ordinary skill in the art may make modifications to the specific implementations and application range according to the idea of the present disclosure. In conclusion, the content of the specification should not be construed as a limitation to the present disclosure.

What is claimed is:

1. A method of opportunistic screening of osteoporosis, comprising:
    obtaining a plain film chest X-ray (CXR);
    extracting regions of interest (ROIs) from the plain film CXR; and
    providing individual bone mineral density (BMD) scores corresponding to the extracted ROIs and a joint BMD corresponding to the plain film CXR based on a multi-ROI model by performing:
        inputting the extracted ROIs into a backbone network to generate individual feature vectors, each individual feature vector corresponding to one of the extracted ROIs;
        concatenating the individual feature vectors into a joint feature vector;
        individually decoding the individual feature vectors by a shared fully connected (FC) layer to generate the individual BMDs, each individual BMD corresponding to one of the individual feature vectors; and
        decoding the joint feature vector by a separate FC layer to generate the joint BMD;
    wherein extracting the ROIs from the plain film CXR includes:
    using a landmark detection method to automatically detect a plurality of landmarks in the plain film CXR; and
    based on the plurality of landmarks, extracting the ROIs from the plain film CXR.

2. The method according to claim 1, before obtaining the plain film CXR, further comprising:
    performing training of the multi-ROI model based on a plurality of plain film CXRs each having a ground truth BMD measured by a dual-energy X-ray absorptiometry (DXA) machine, wherein the training of the multi-ROI model includes calculating mean squared errors (MSEs) on each of the individual BMDs and the joint BMD, and an average MSE thereof being used as a training loss.

3. The method according to claim 2, wherein:
    the ground truth BMD corresponding to each plain film CXR is measured by the DXA machine for spine bones or hip bones;
    in response to the multi-ROI model being trained based on the ground truth BMD for the spine bones, the BMD predicted by the multi-ROI model is the BMD for the spine bones; and in response to the multi-ROI model being trained based on the ground truth BMD for the hip bones, the BMD predicted by the multi-ROI model is the BMD for the hip bones.

4. The method according to claim 3, further comprising: performing an opportunistic screening of osteoporosis on a test plain film CXR, comprising:
   extracting ROIs from the test plain film CXR;
   providing a BMD corresponding to the test plain film CXR based on the trained multi-ROI model by performing:
      inputting the extracted ROIs into the backbone network to generate individual feature vectors, each individual feature vector corresponding to one of the extracted ROIs, and concatenating the individual feature vectors into a joint feature vector; and
      decoding the joint feature vector by the separate FC layer to generate the joint BMD, the joint BMD being the BMD corresponding to the test plain film CXR;
   converting the BMD corresponding to the test plain film CXR into a T-score; and
   in response to the T-score being smaller than or equal to a T-score threshold, determining a positive diagnosis of osteoporosis.

5. The method according to claim 1, before extracting the ROIs from the plain film CXR, further comprising:
   resizing the plain film CXR to a fixed size.

6. The method according to claim 1, wherein:
   the backbone network is a visual geometry group 16-layer (VGG-16) neural network.

7. The method according to claim 1, wherein:
   the ROIs include a plurality of local regions in the plain film CXR and a global region including the entire plain film CXR.

8. A system of opportunistic screening of osteoporosis, comprising:
   a memory storing a computer program; and
   a processor configured to execute the computer program stored in the memory to:
      obtain a plain film chest X-ray (CXR);
      extract regions of interest (ROIs) from the plain film chest x-ray; and
      provide individual bone mineral density (BMD) scores corresponding to the extracted ROIs and a joint BMD corresponding to the plain film CXR based on a multi-ROI model by performing:
         inputting the extracted ROIs into a backbone network to generate individual feature vectors, each individual feature vector corresponding to one of the extracted ROIs;
         concatenating the individual feature vectors into a joint feature vector;
         individually decoding the individual feature vectors by a shared fully connected (FC) layer to generate the individual BMDs, each individual BMD corresponding to one of the individual feature vectors; and
         decoding the joint feature vector by a separate FC layer to generate the joint BMD;
   wherein when extracting the ROIs from the plain film CXR, the processor is further configured to:
   use a landmark detection method to automatically detect a plurality of landmarks in the plain film CXR; and
   based on the plurality of landmarks, extract the ROIs from the plain film CXR.

9. The system according to claim 8, wherein before obtaining the plain film CXR, the processor is further configured to:
   performing training of the multi-ROI model based on a plurality of plain film CXRs each having a ground truth BMD measured by a dual-energy X-ray absorptiometry (DXA) machine, wherein the training of the multi-ROI model includes calculating mean squared errors (MSEs) on each of the individual BMDs and the joint BMD, and an average MSE thereof being used as a training loss.

10. The system according to claim 9, wherein:
    the ground truth BMD corresponding to each plain film CXR is measured by the DXA machine for spine bones or hip bones;
    in response to the multi-ROI model being trained based on the ground truth BMD for the spine bones, the BMD predicted by the multi-ROI model is the BMD for the spine bones; and
    in response to the multi-ROI model being trained based on the ground truth BMD for the hip bones, the BMD predicted by the multi-ROI model is the BMD for the hip bones.

11. The system according to claim 10, wherein the processor is further configured to:
    perform an opportunistic screening of osteoporosis on a test plain film CXR, comprising:
       extracting ROIs from the test plain film CXR;
       providing a BMD corresponding to the test plain film X-ray image based on the trained multi-ROI model by performing:
          inputting the extracted ROIs into the backbone network to generate individual feature vectors, each individual feature vector corresponding to one of the extracted ROIs, and concatenating the individual feature vectors into a joint feature vector; and
          decoding the joint feature vector by the separate FC layer to generate the joint BMD, the joint BMD being the BMD corresponding to the test plain film CXR;
       converting the BMD corresponding to the test plain film CXR into a T-score; and
       in response to the T-score being smaller than or equal to a T-score threshold, determining a positive diagnosis of osteoporosis.

12. The system according to claim 8, wherein before extracting the ROIs from the plain film CXR, the processor is further configured to:
    resize the plain film CXR to a fixed size.

13. The system according to claim 8, wherein:
    the backbone network is a visual geometry group 16-layer (VGG-16) neural network.

14. The system according to claim 8, wherein:
    the ROIs include a plurality of local regions in the plain film CXR and a global region including the entire plain film CXR.

15. A non-transitory computer-readable storage medium storing a computer program, when being executed by a processor, the computer program performing:
    obtaining a plain film chest X-ray (CXR);
    extracting regions of interest (ROIs) from the plain film CXR; and
    providing individual bone mineral density (BMD) scores corresponding to the extracted ROIs and a joint BMD corresponding to the plain film CXR based on a multi-ROI model by performing:

inputting the extracted ROIs into a backbone network to generate individual feature vectors, each individual feature vector corresponding to one of the extracted ROIs;
concatenating the individual feature vectors into a joint feature vector;
individually decoding the individual feature vectors by a shared fully connected (FC) layer to generate the individual BMDs, each individual BMD corresponding to one of the individual feature vectors; and
decoding the joint feature vector by a separate FC layer to generate the joint BMD;
wherein extracting the ROIs from the plain film CXR includes:
using a landmark detection method to automatically detect a plurality of landmarks in the plain film CXR; and
based on the plurality of landmarks, extracting the ROIs from the plain film CXR.

16. The non-transitory computer-readable storage medium according to claim 15, before obtaining the plain film CXR, the computer program further performing:
performing training of the multi-ROI model based on a plurality of plain film CXRs each having a ground truth BMD measured by a dual-energy X-ray absorptiometry (DXA) machine, wherein the training of the multi-ROI model includes calculating mean squared errors (MSEs) on each of the individual BMDs and the joint BMD, and an average MSE thereof being used as a training loss.

17. The non-transitory computer-readable storage medium according to claim 16, wherein:
the ground truth BMD corresponding to each plain film CXR is measured by the DXA machine for spine bones or hip bones;
in response to the multi-ROI model being trained based on the ground truth BMD for the spine bones, the BMD predicted by the multi-ROI model is the BMD for the spine bones; and
in response to the multi-ROI model being trained based on the ground truth BMD for the hip bones, the BMD predicted by the multi-ROI model is the BMD for the hip bones.

18. The non-transitory computer-readable storage medium according to claim 17, the computer program further performing:
performing an opportunistic screening of osteoporosis on a test plain film CXR, comprising:
extracting ROIs from the test plain film CXR;
providing a BMD corresponding to the test plain film CXR based on the trained multi-ROI model by performing:
inputting the extracted ROIs into the backbone network to generate individual feature vectors, each individual feature vector corresponding to one of the extracted ROIs, and concatenating the individual feature vectors into a joint feature vector; and
decoding the joint feature vector by the separate FC layer to generate the joint BMD, the joint BMD being the BMD corresponding to the test plain film CXR;
converting the BMD corresponding to the test plain film CXR into a T-score; and
in response to the T-score being smaller than or equal to a T-score threshold, determining a positive diagnosis of osteoporosis.

\* \* \* \* \*